United States Patent
Ikeda et al.

(10) Patent No.: US 8,519,600 B2
(45) Date of Patent: Aug. 27, 2013

(54) ULTRASONIC TRANSDUCER

(75) Inventors: Masako Ikeda, Osaka (JP); Takashi Ogura, Osaka (JP)

(73) Assignee: Panasonic Corporation, Osaka (JP)

( * ) Notice: Subject to any disclaimer, the term of this patent is extended or adjusted under 35 U.S.C. 154(b) by 279 days.

(21) Appl. No.: 13/060,704

(22) PCT Filed: Jun. 4, 2010

(86) PCT No.: PCT/JP2010/003746
§ 371 (c)(1),
(2), (4) Date: Feb. 25, 2011

(87) PCT Pub. No.: WO2010/143387
PCT Pub. Date: Dec. 16, 2010

(65) Prior Publication Data
US 2011/0152691 A1 Jun. 23, 2011

(30) Foreign Application Priority Data
Jun. 8, 2009 (JP) ................... 2009-136966

(51) Int. Cl.
*B06B 1/06* (2006.01)
(52) U.S. Cl.
CPC .................... *B06B 1/0677* (2013.01)
USPC .......................... 310/334; 310/326
(58) Field of Classification Search
CPC ....................................... B06B 1/06
USPC ................ 310/322, 326, 327, 334, 335
See application file for complete search history.

(56) References Cited

U.S. PATENT DOCUMENTS 7,808,157 B2 * 10/2010 Oakley et al. ............ 310/334
2008/0139945 A1 6/2008 Hu

FOREIGN PATENT DOCUMENTS

| JP | 7-131895 | 5/1995 |
| JP | 8-182094 | 7/1996 |
| JP | 9-278414 | 10/1997 |
| JP | 2001-321659 | 11/2001 |
| JP | 2003-190162 | 7/2003 |
| JP | 2009-82567 | 4/2009 |
| WO | 2006/062164 | 6/2006 |

OTHER PUBLICATIONS

International Search Report issued Sep. 7, 2010 in corresponding International Application No. PCT/JP2010/003746.

* cited by examiner

*Primary Examiner* — Derek Rosenau
(74) *Attorney, Agent, or Firm* — Wenderoth, Lind & Ponack, L.L.P.

(57) ABSTRACT

An ultrasonic transducer includes: a piezoelectric transducer (1) emitting ultrasonic waves; and a backing layer (4) provided in contact with a back side of the piezoelectric transducer (1) and attenuating ultrasonic waves that are emitted toward the back side of the piezoelectric transducer (1) and have an opposite phase to the phase of ultrasonic waves emitted toward a front side of the piezoelectric transducer (1). The acoustic tubes (5) are disposed in the backing layer (4) such that a longitudinal direction of each acoustic tube (5) is in line with a traveling direction of the ultrasonic waves emitted by the piezoelectric transducer (1) toward the front and the back side. The acoustic tubes (5) have mutually different lengths on the basis of a principle of an acoustic wave synthesis, and attenuate in whole or in part the ultrasonic waves emitted by the piezoelectric transducer (1) toward the backing layer (4).

13 Claims, 12 Drawing Sheets

Amount of microballoons mixed in each layer is controlled, and allow microballoons in each layer to reflect ultrasonic waves

ULTRASONIC TRANSDUCER

TECHNICAL FIELD

The present invention relates to ultrasonic transducers used for ultrasonic diagnosis.

BACKGROUND ART

Figure 1:
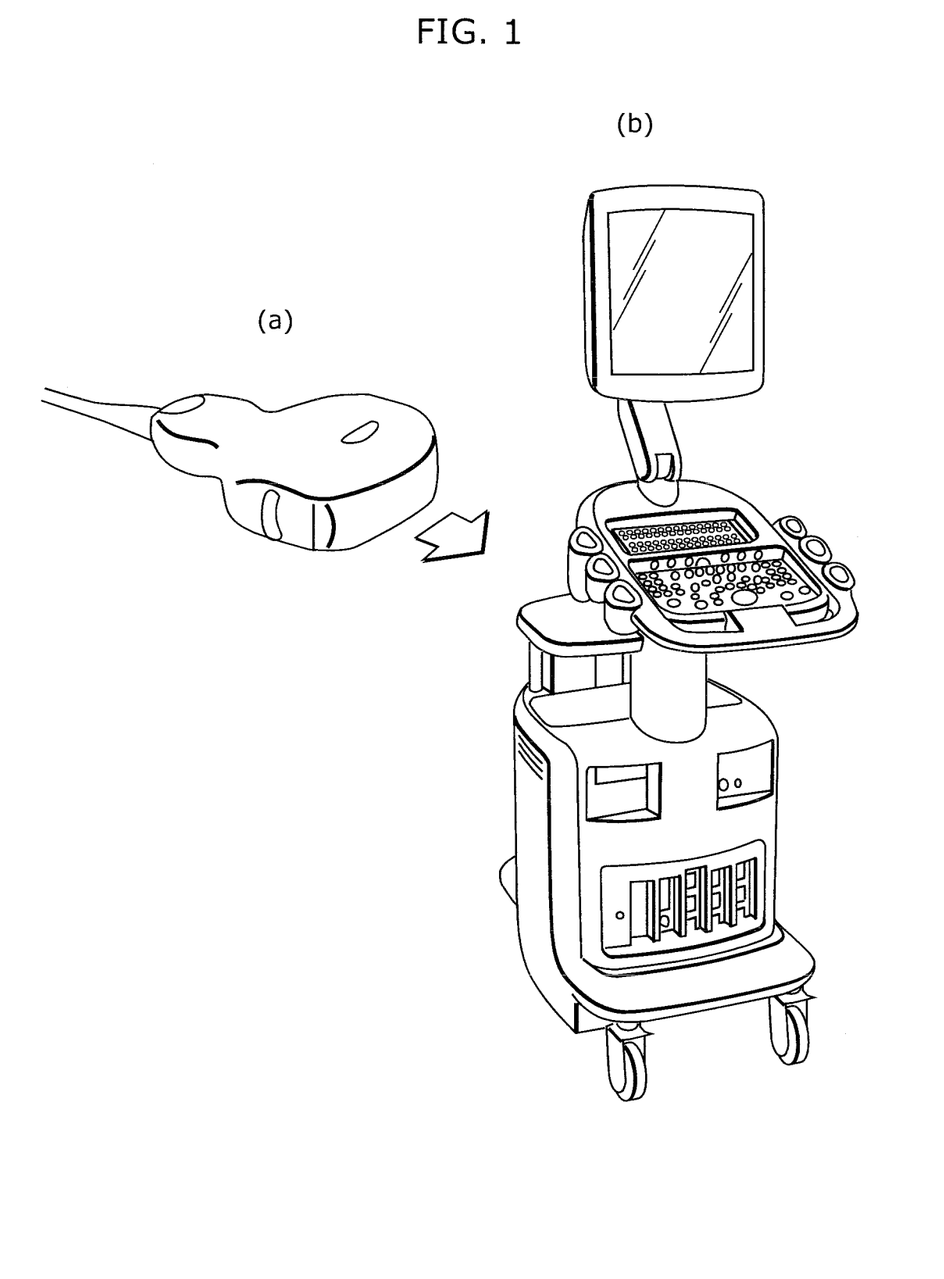

FIG. 1 shows an exemplary appearance of an ultrasonic transducer and an ultrasonic diagnostic apparatus. As shown in FIG. 1 (a), the ultrasonic transducer is connected to the ultrasonic diagnostic apparatus by a cable. The ultrasonic transducer transmits ultrasonic waves in the direction of an arrow shown in the figure, and receives reflection waves which are reflected from a living body and is in the opposite direction of the arrow. As shown in FIG. 1 (b), the ultrasonic diagnostic apparatus performs image analysis on the reflected waves received by the ultrasonic transducer, and displays on a monitor an image of the inside of the living body obtained through the analysis.

When such an ultrasonic transducer transmits the ultrasonic waves from a piezoelectric transducer, the ultrasonic waves are emitted not only to the front side of a transducer, but also to the back side of the transducer.

Figure 2:
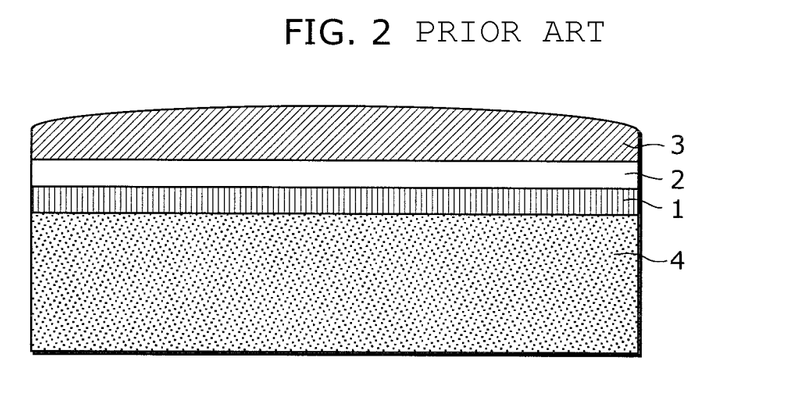
FIG. 2 is a cross-sectional view of a conventional ultrasonic transducer.

Here, an example of a conventional ultrasonic transducer is described with reference to a drawing. FIG. 2 is a vertical cross-sectional view for showing a structure of the conventional ultrasonic transducer. FIG. 2 shows the structure in which, from the top, an acoustic lens 3, a matching layer 2, a piezoelectric transducer 1, and a backing layer 4 are stacked.

In typical ultrasonic diagnostic apparatus, the ultrasonic waves transmitted from the piezoelectric transducer 1 passes through the matching layer 2 and the acoustic lens 3, and then emitted into a living body. As a result, the ultrasonic waves reflected within the living body pass through the same route in the reverse order as the outgoing ultrasonic waves passed, and then received back by the piezoelectric transducer 1. Depending on the strength of reception or response time, a received signal is visualized in shading by the ultrasonic diagnostic apparatus.

On the other hand, as described in the beginning, ultrasonic waves having an opposite phase to the phase of ultrasonic waves that are emitted to the front are emitted from the piezoelectric transducer 1 to the back at the same time. The ultrasonic waves emitted to the back side of the piezoelectric transducer 1 are attenuated by the backing layer 4. However, when the backing layer 4 is formed of the material which does not sufficiently attenuate the ultrasonic waves emitted to the back side, the ultrasonic waves having the opposite phase can reflect within the backing layer 4 and can go back toward the piezoelectric transducer 1.

Due to the effect of the reflected waves described above, noise is superimposed on the received ultrasonic wave signal, resulting in a deteriorated ultrasonic wave resolution of the ultrasonic diagnostic apparatus.

In general, the ultrasonic transducer includes in the backing layer 4 a material having internal loss and distance that can provide adequate attenuation to the ultrasonic waves emitted to the back side, and thus enables the ultrasonic diagnostic apparatus to maintain satisfactory ultrasonic wave resolution. However, such a conventional method has a disadvantage of increasing the thickness of the backing layer itself.

Furthermore in Patent Literature (PTL) 1, in order to decrease the thickness of the backing layer 4, a heat release block is disposed on the back side of the backing layer 4, thereby attenuating the ultrasonic waves emitted to the back side of the piezoelectric transducer 1.

CITATION LIST

Patent Literature

International Publication WO 2006/062164

SUMMARY OF INVENTION

Technical Problem

However, with the conventional structure, the problem of thickening of the backing layer 4 cannot be avoided. Furthermore, even when the heat release block is provided on the back side of the backing layer 4 so that the thickness of the backing layer 4 is decreased, such a structure requires the heat release block in addition to the backing layer 4. Thus, as a whole, the thickness of the structure for attenuating the ultrasonic waves cannot be easily decreased. Further, the use of the heat release block causes a problem of increasing the cost of manufacturing the ultrasonic transducer as it requires material other than the backing layer.

The present invention has been devised to solve the above conventional problems, and has an object of realizing the ultrasonic transducer with a good sensitivity by effectively attenuating in the backing layer the ultrasonic waves emitted by the piezoelectric transducer to the back side, and reducing the reflected waves that are returning from the back side to the transducer side. In addition, it is intended to significantly reduce the thickness of the backing layer compared with the conventional backing layer.

Solution to Problem

In order to solve the above conventional problems, the ultrasonic transducer according to the present invention includes a vibrating element, and a backing material which is provided in contact with the back side of the vibrating element. The backing material attenuates ultrasonic waves that are emitted toward the back side of the vibrating element which have an opposite phase to the phase of ultrasonic waves emitted toward the front side of the vibrating element. In the backing material, acoustic tubes are disposed such that a longitudinal direction of each of the acoustic tubes is in line with a traveling direction of the ultrasonic waves which are emitted by the vibrating element and travel toward the front side and the back side. The acoustic tubes have mutually different lengths on the basis of a principle of an acoustic wave synthesis, and the acoustic tubes attenuate in whole or in part the ultrasonic waves emitted by the vibrating element toward the backing material.

The ultrasonic transducer according to the present invention includes, in the backing layer disposed on the back side of the piezoelectric transducer, a single acoustic tube or a plurality of acoustic tubes having a sufficiently short width comparing with a wavelength of the ultrasonic waves emitted (a half-wave length at maximum). The length of the acoustic tube is set according to the wavelength of the ultrasonic waves to be emitted, so that incident waves and reflected waves interfere with and cancel out each other.

With the above structure, the ultrasonic waves, which are the ultrasonic waves output from the back side of the piezoelectric transducer that returns after having reflected off the end of the backing layer, is canceled out by the acoustic tube. As a result, it is possible to realize the ultrasonic transducer in which the noise can be effectively reduced, heat generation is suppressed, received signal is unaffected, and the backing layer is thin.

Advantageous Effects of Invention

The ultrasonic transducer according to the present invention effectively reduces the reflected waves by cancelling out the reflected waves, which are the ultrasonic waves that return after having reflected off the end of the backing layer. Thus, the ultrasonic transducer makes it possible to obtain a good ultrasonic wave image without noise.

In addition, a structure of the ultrasonic transducer according to the present invention allows the backing layer to be thin, and thus the cost in terms of material can be reduced, and the thickness of the ultrasonic transducer can be decreased. Further, in the ultrasonic transducer according to the present invention, heat generation is suppressed, which allows a higher output intensity, and accordingly, an apparent sensitivity is increased.

BRIEF DESCRIPTION OF DRAWINGS

FIGS. 1 (a) and (b) are diagrams which show an exemplary appearance of an ultrasonic transducer and an ultrasonic diagnostic apparatus.

FIG. 8 (a) to (d) are a perspective view and a three-view drawing which show a three-dimensional structure of one-dimensionally arranged acoustic tubes.

FIG. 9 (a) to (d) are a perspective view and a three-view drawing which show a three-dimensional structure of two-dimensionally arranged acoustic tubes.

FIGS. 10 (a) and (b) are cross-sectional views showing which of planes is in contact with the other layer, one of the planes having openings of the acoustic tubes formed within the backing layer, and the other of the planes not having the openings of the acoustic tubes formed within the backing layer.

FIGS. 12 (a) and (b) are diagrams showing a method of forming a backing layer in which microcapsules are used as acoustic tubes.

DESCRIPTION OF EMBODIMENTS

Hereinafter, embodiments of the present invention will be described with reference to the drawings.

Embodiment 1

Figure 3:
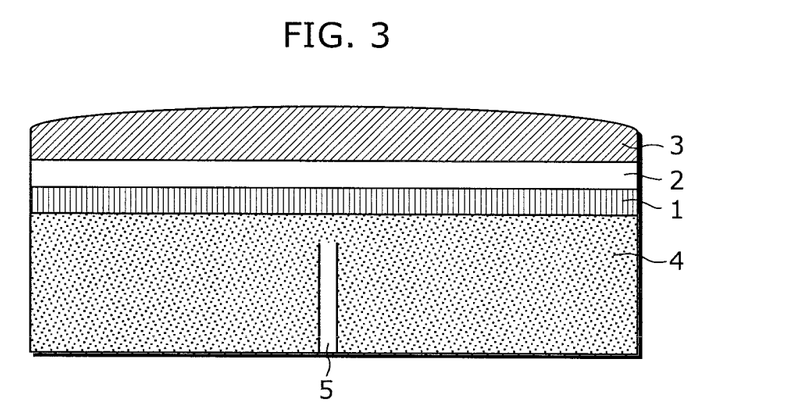
FIG. 3 is a cross-sectional view of an ultrasonic transducer which includes a backing layer including a single acoustic tube according to Embodiment 1 of the present invention.

FIG. 3 is a cross-sectional view of an ultrasonic transducer according to Embodiment 1 of the present invention. As shown in FIG. 3, the ultrasonic transducer according to Embodiment 1 includes a piezoelectric transducer 1, a matching layer 2, an acoustic lens 3, and a backing layer 4.

As shown in FIG. 3, the ultrasonic transducer according to this embodiment includes an acoustic tube 5 disposed within the backing layer 4. The acoustic tube 5 is formed such that its width is sufficiently small comparing with the wavelength of the ultrasonic waves emitted by the piezoelectric transducer 1, and such that its length causes direct waves of the ultrasonic waves and reflected waves of the ultrasonic waves to cancel out each other.

For example, when the backing layer 4 is formed of an epoxy resin and it is assumed that the ultrasonic waves f emitted by the piezoelectric transducer 1 is 5 MHz, the wavelength λ in the backing layer 4 may be obtained by Equation 1.

[Math. 1]

$$\lambda = \frac{C}{f} \qquad \text{(Equation 1)}$$

When it is assumed that speed of sound c within the epoxy resin is 5000 m/s, the wavelength of the ultrasonic waves is obtained as λ=1000 μm. In this case, when the length Ln of the acoustic tube 5 is 250 μm, a phase of the reflected waves shifts by ¼ causing the direct waves and the reflected waves to cancel out each other. Furthermore, in this case, the width w of the acoustic tube 5 needs to satisfy w<Ln so that a rectilinear propagation of acoustic waves is maintained.

In the backing layer 4 with the acoustic tube 5 described above, the ultrasonic waves emitted to the back side by the piezoelectric transducer 1 are attenuated, thereby allowing the ultrasonic transducer to receive only the ultrasonic waves that are reflected from the front side. As a result, sensitivity of an ultrasonic wave signal is increased and thus a good image can be obtained.

Embodiment 2

Figure 4:
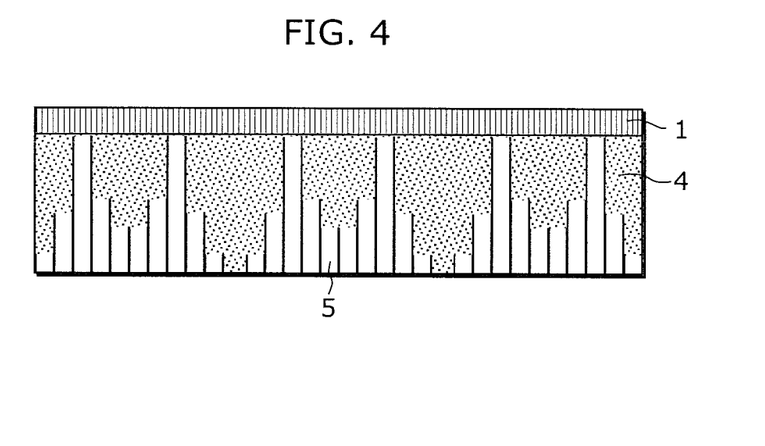
FIG. 4 is a cross-sectional view of an ultrasonic transducer which includes a backing layer including acoustic tubes according to Embodiment 2 of the present invention.

FIG. 4 is a cross-sectional view of the backing layer 4 according to Embodiment 2 of the present invention. Acoustic tubes 5 are disposed within the backing layer 4.

Figure 5:
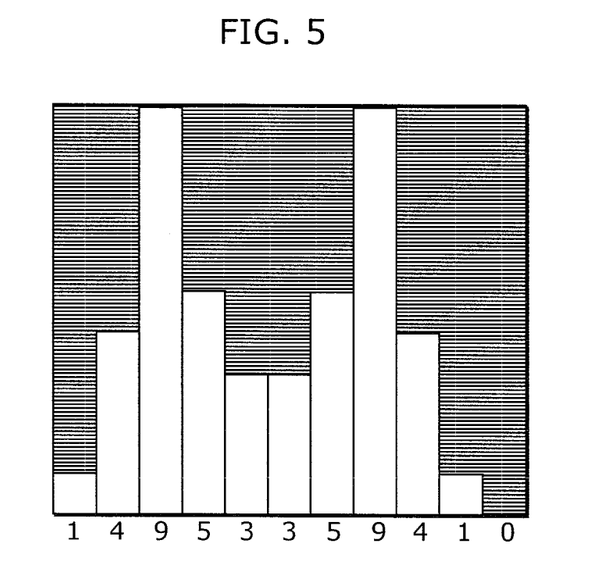
FIG. 5 is a cross-sectional view of an exemplary backing layer including acoustic tubes arranged on the basis of a quadratic residue sequence according to Embodiment 2 of the present invention.

FIG. 5 is a cross-sectional view of an exemplary arrangement of the acoustic tubes 5 according to Embodiment 2. Shown in the figure is an example of a backing layer in which the acoustic tubes 5 are arranged on the basis of a quadratic residue sequence. Length Ln of each acoustic tube is determined by a one dimensional quadratic residue sequence shown in Equation 2 below.

[Math. 2]

$$Ln = \frac{c \cdot n^2 (\text{mod } N)}{2N\omega r} \quad \text{(Equation 2)}$$

Here, c denotes a speed of sound, N denotes a prime number, and n denotes an integer which varies in a range of 0 to (N−1), and ωr denotes any design frequency. For example when it is assumed that the speed of sound c within the epoxy resin is 5000 m/s, N=11, and ωr=5 MHz, each acoustic tube 5 has, with 45.5 μm as unit length "1", a length of 1, 4, 9, 5, 3, 3, 5, 9, 4, 1, and 0 respectively.

Figure 7:
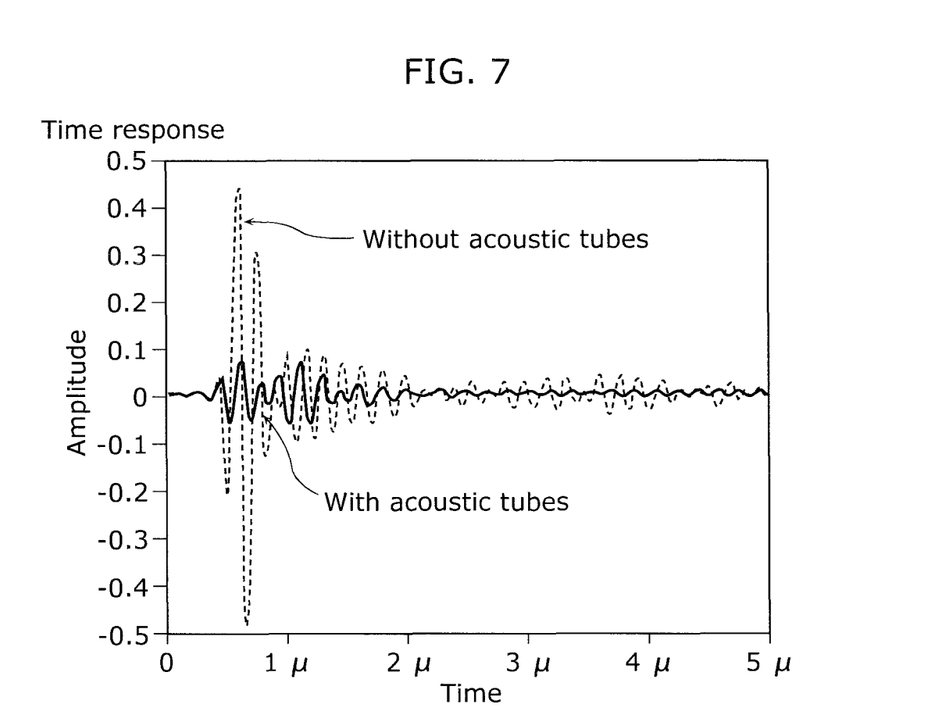
FIG. 7 shows a comparison in the amplitude changes of noise contained in a signal between in the case where the backing layer includes acoustic tubes and in the case where the backing layer does not include acoustic tubes.

The acoustic tubes 5 disposed according to the arrangement described above are known to absorb and spread the acoustic waves of broadband because a discontinuity of phase occurs in the vicinity of an opening of each of adjacent acoustic tubes 5, and the acoustic tubes 5 can reduce the reflected waves within the backing layer 4. An example of an effect of disposing acoustic tubes 5 as described above is shown in FIG. 7. FIG. 7 shows a comparison in the amplitude changes of noise contained in a signal between in the case where the backing layer includes acoustic tubes and in the case where the backing layer does not include acoustic tubes.

Figure 6:
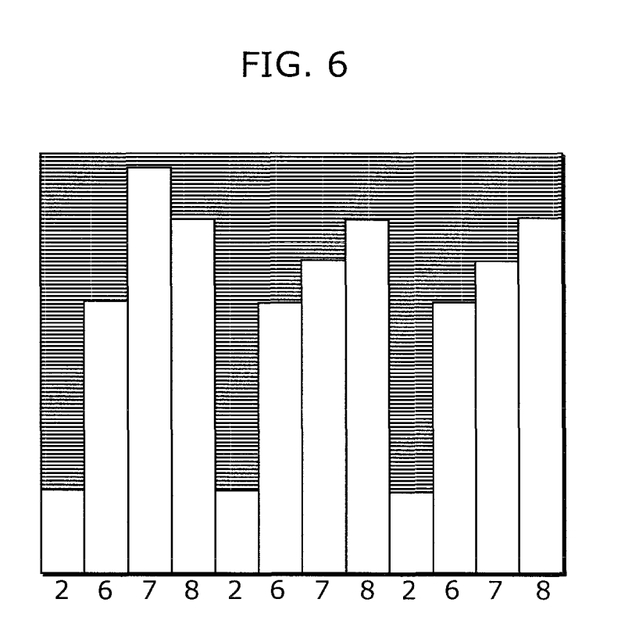
FIG. 6 is a cross-sectional view of an exemplary backing layer which includes acoustic tubes arranged on the basis of a primitive root sequence according to Embodiment 2 of the present invention.

Furthermore, determining the length Ln of each acoustic tube 5 by a primitive root sequence shown in Equation 3 below can also produce the similar effect.

[Math. 3]

$$Ln = \frac{c \cdot r^n (\text{mod } N)}{2(N-1)\omega r} \quad \text{(Equation 3)}$$

Figure 8:
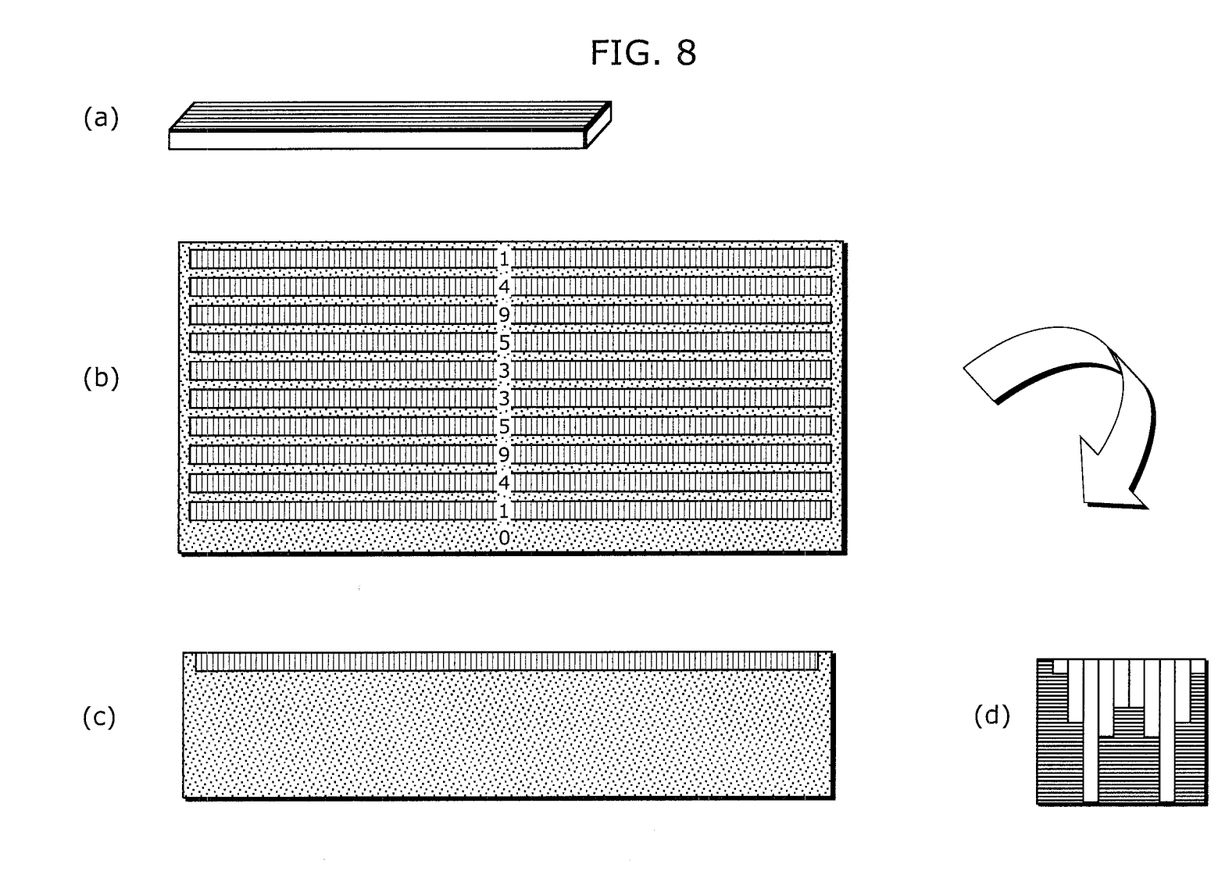

Here, c denotes a speed of sound, N denotes a prime number, and n denotes an integer which varies in a range of 0 to (N−1), r denotes a primitive root of N, and ωr denotes any design frequency. FIG. 6 is a cross-sectional view of an exemplary arrangement of the acoustic tubes 5 when N=11 and r=2. Shown in the figure is an example of the backing layer in which the acoustic tubes 5 are arranged on the basis of the primitive root sequence. Note that the arrangement of the acoustic tubes 5 shown in FIG. 5 and FIG. 6 is not limited to a one-dimensional arrangement, and a two-dimensional arrangement may also be used. FIG. 8 (a) to (d) are perspective view and a three-view drawing which show a three-dimensional structure of one-dimensionally arranged acoustic tubes. FIG. 8 (a) is a perspective view showing the backing layer 4 in which the one-dimensionally arranged acoustic tubes 5 are formed according to the arrangement shown in FIG. 5. For example, as shown in FIG. 8 (b), grooves which are parallel in the horizontal direction are formed in the backing layer 4. The grooves are formed to have a depth of 1, 4, 9, 5, 3, 3, 5, 9, 4, 1, and 0 in sequence in the vertical direction. As shown in a front elevation view in FIG. 8 (c), each single groove is a groove having a uniform depth. When the backing layer 4 is cut along a plane perpendicular to a longitudinal direction of the grooves, the depth of each groove is arranged in the quadratic residue sequence as shown in FIG. 8 (d).

Figure 9:
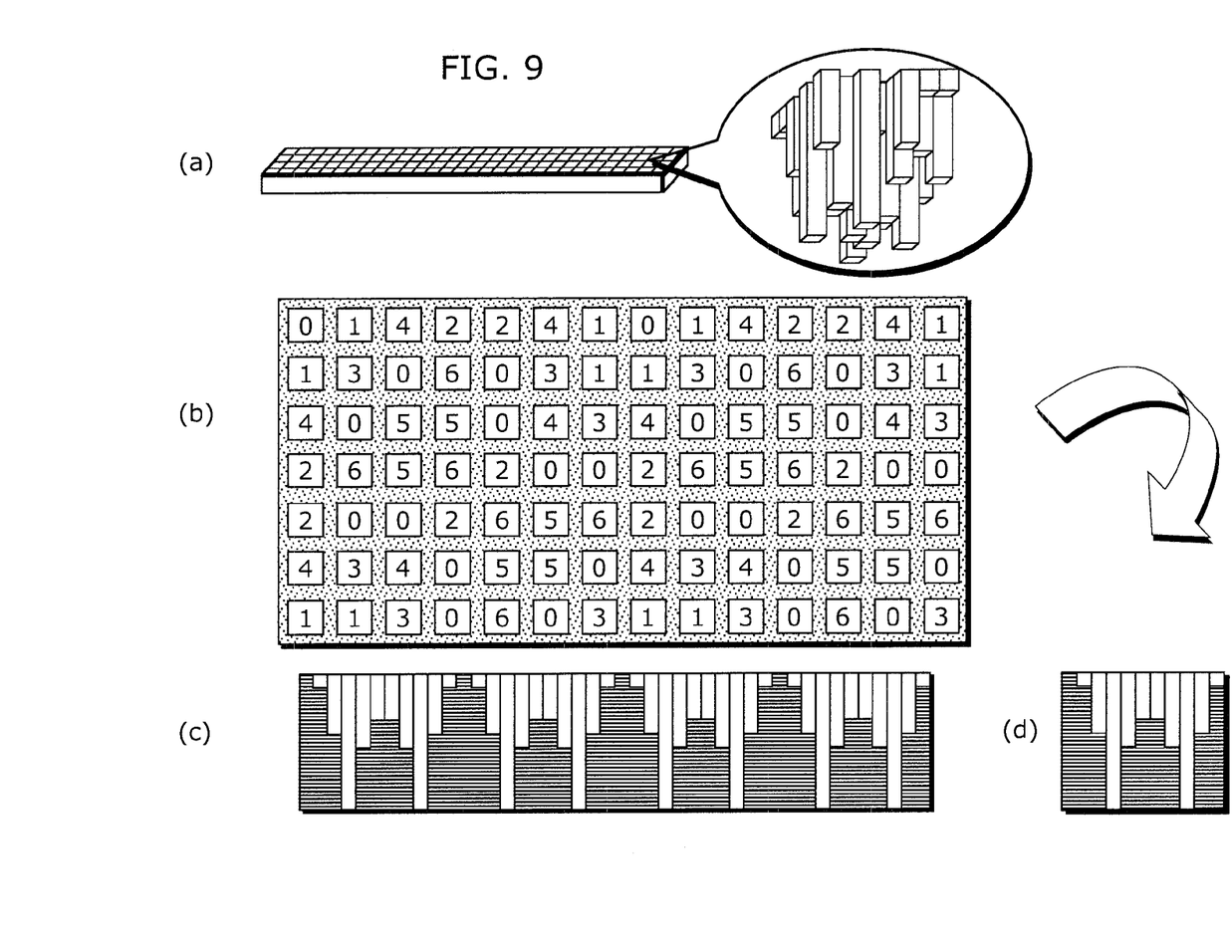

FIG. 9 (a) to (d) are a perspective view and a three-view drawing showing a three-dimensional structure of two-dimensionally arranged acoustic tubes. FIG. 9 (a) is a perspective view showing the backing layer 4 in which two-dimensionally arranged acoustic tubes 5 are formed. For example, as shown in FIG. 9 (b), in the backing layer 4, grooves are formed to have various depths in two-dimensional directions, horizontal direction and vertical direction. In the case where c=5000 m/s, N=7, and ωr=5 MHz, the grooves are formed to have a depth of integer multiple of a unit length of 71.5 μm. As shown in FIGS. 9 (c) and (d), the grooves are arranged such that the depths of the grooves are repeated in a predetermined pattern when viewed from the direction perpendicular to the cross-section as well as when viewed from the direction horizontal to the cross-section.

Figure 10:
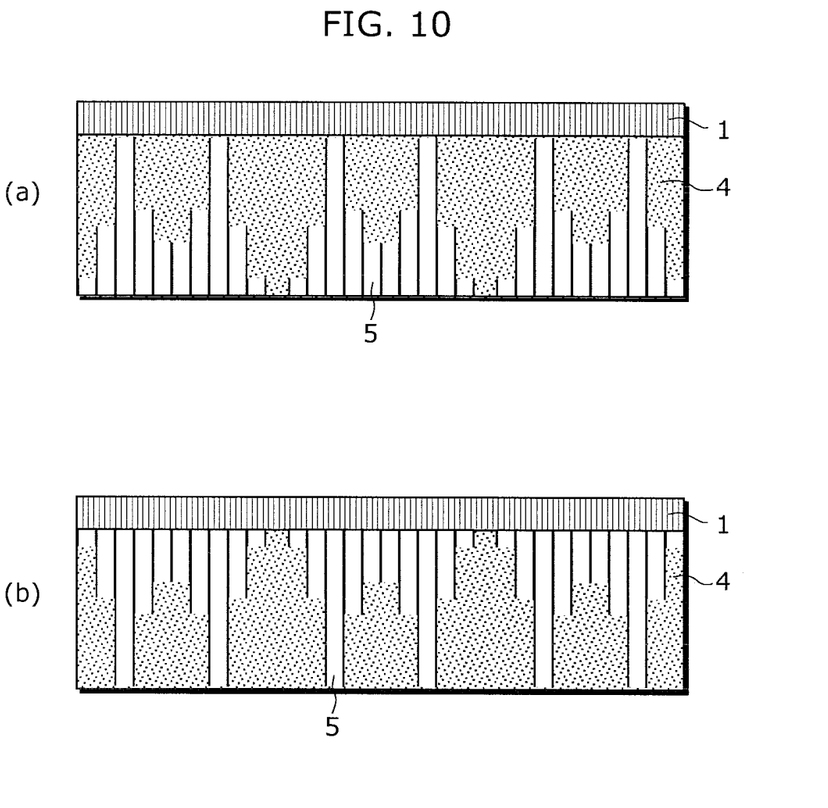

FIGS. 10 (a) and (b) are cross-sectional views showing which of planes is in contact with the piezoelectric transducer 1, one of the planes having openings of the acoustic tubes formed within the backing layer, and the other of the planes not having the openings of the acoustic tubes formed within the backing layer. FIG. 10 (a) shows an example in which the plane of the backing layer 4 without the openings of the acoustic tubes 5 is in contact with the layer of the piezoelectric transducer 1. In addition, FIG. 10 (b) shows an example in which the plane of the backing layer 4 with the openings of the acoustic tubes 5 is in contact with the layer of the piezoelectric transducer 1. When acoustic tubes 5 are to be used to cancel out the reflected waves which are the ultrasonic waves that returns after having reflected off the end of the backing layer 4, the plane having the openings of the acoustic tubes 5 may be placed at either side of the piezoelectric transducer 1, that is to say, the acoustic tubes 5 may be formed as shown in FIG. 10 (a) and may also be formed as shown in FIG. 10 (b).

Figure 11:
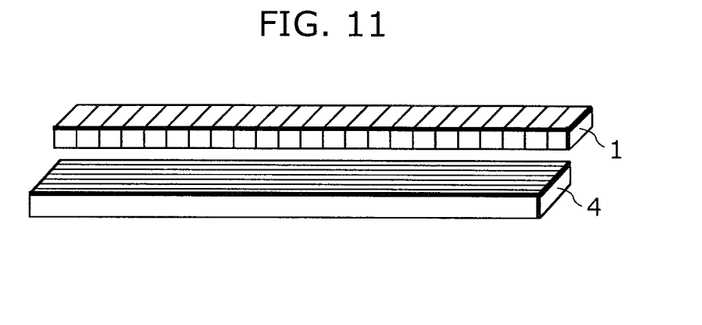
FIG. 11 is a diagram showing a relation between a direction of dice cutting of the piezoelectric transducer, and a direction of formation of one-dimensionally arranged acoustic tubes that are formed within the backing layer.

FIG. 11 is a diagram showing a relation between a direction of dice cutting of the piezoelectric transducer, and a direction of formation of one-dimensionally arranged acoustic tubes formed within the backing layer. As shown in the figure, the one-dimensionally arranged acoustic tubes 5 within the backing layer 4 are formed such that a direction of dice cutting of the piezoelectric transducer 1 and a longitudinal direction of the grooves of the acoustic tubes 5 are at right angles to each other, so that a larger number of the acoustic tubes of different lengths act on the piezoelectric transducer of 1 ch. Thus, the reflected waves can be reduced more effectively within the backing layer 4.

Embodiment 3

Figure 14A:
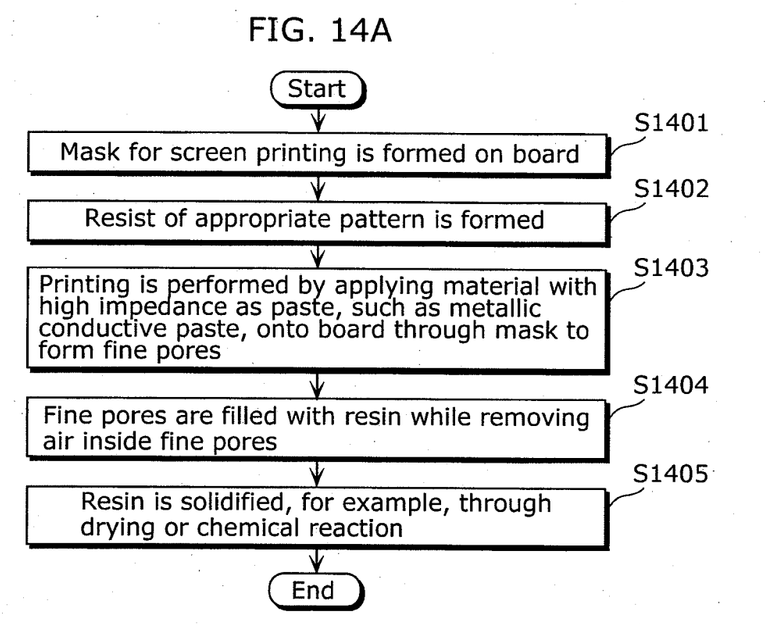
FIG. 14A is a flowchart showing steps for forming a backing layer using screen printing.

In order to realize the backing layer 4 according to Embodiment 3, relief of 250 μm is formed on a board by precision printing based on Embodiment 1. Here, the longitudinal direction of the acoustic tube corresponds to the direction of thickness of ink to be printed. FIG. 14A is a flowchart showing steps for forming the backing layer using screen printing. More specifically, first, a mask for screen printing which is adjusted to have the thickness of 250 μm when dried is formed on a board (S1401). Next, a resist for printing a predetermined pattern is formed (S1402), and then printing is performed by applying material with high impedance as paste, such as metallic conductive paste, onto the board through the mask (S1403). As a result, fine pores are formed on the board. It is to be noted that, here, it is necessary to keep the thickness of the printed paste to be 250 μm or less. When the thickness is 250 μm or less, the rectilinear propagation of the acoustic waves which enter the fine pores is good, and thus the reflected waves are reduced in highly effective manner. However, it is not that the effect disappears suddenly once the thickness exceeds 250 μm. Therefore, as far as a desired effect is achieved, the thickness of the printed paste does not necessarily have to be exactly 250 μm or less.

In order to facilitate a reflection of the acoustic waves, it is preferable that the board on which the printing is performed is made of a material with acoustic impedance equivalent to or similar to the acoustic impedance of the conductive paste used for the printing. Next, a resin material with low acoustic impedance is applied into the formed fine pores, and a squeegee or the like is used to fill the fine pores with the resin while completely removing air inside the fine pores (S1404).

By solidifying the resin material, for example through drying or reaction, a backing material which reduces the reflected waves effectively at 5 MHz can be obtained (S1405).

Embodiment 4

Figure 14B:
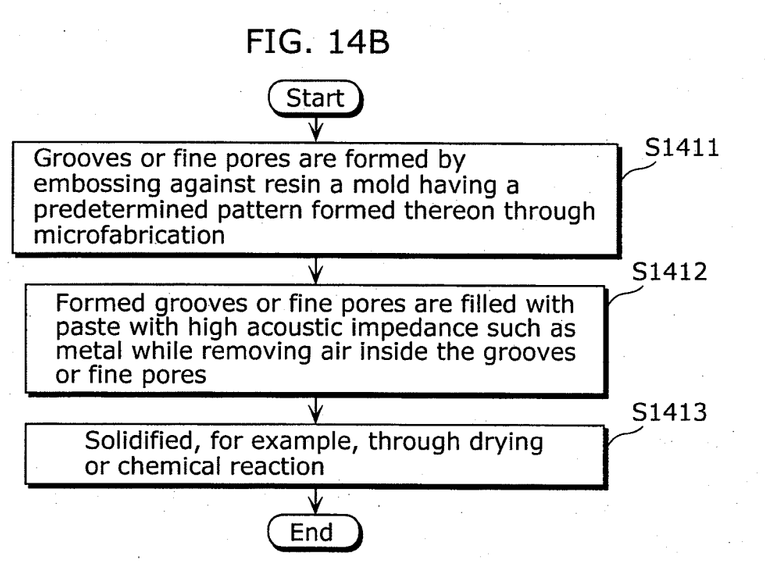
FIG. 14B is a flowchart showing steps for forming a backing layer through embossing using a precise mold that is used in techniques such as nanoimprint.

A backing layer 4 according to Embodiment 4 is realized by a technique in which a precise mold that is used in, for instance, nanoimprint, that is, a mold having a predetermined pattern formed thereon through microfabrication is embossed against a resin. With this, by forming on a board grooves or fine pores each of which has a bore diameter no larger than 250 μm, the backing layer 4 according to Embodiment 4 can be obtained. FIG. 14B is a flowchart showing steps for forming the backing layer through embossing using the precise mold that is used in techniques such as nanoimprint. More specifically, the mold having a predetermined pattern formed thereon through microfabrication is embossed against the resin so that the grooves or fine pores are formed on the board (S1411).

Due to the same reason described in Embodiment 3, the bore diameter does not necessarily have to be 250 μm or less. In the pattern, the conducting path through which the acoustic waves propagate needs to be formed in a shape of convex.

Further, the formed grooves or fine pores are filled with paste with high acoustic impedance such as metal using a squeegee or the like while completely removing air inside the grooves or fine pores (S1412).

By solidifying this material, for example through drying or reaction, a backing material which reduces the reflected waves effectively at 5 MHz can be obtained (S1413).

Embodiment 5

Figure 12:
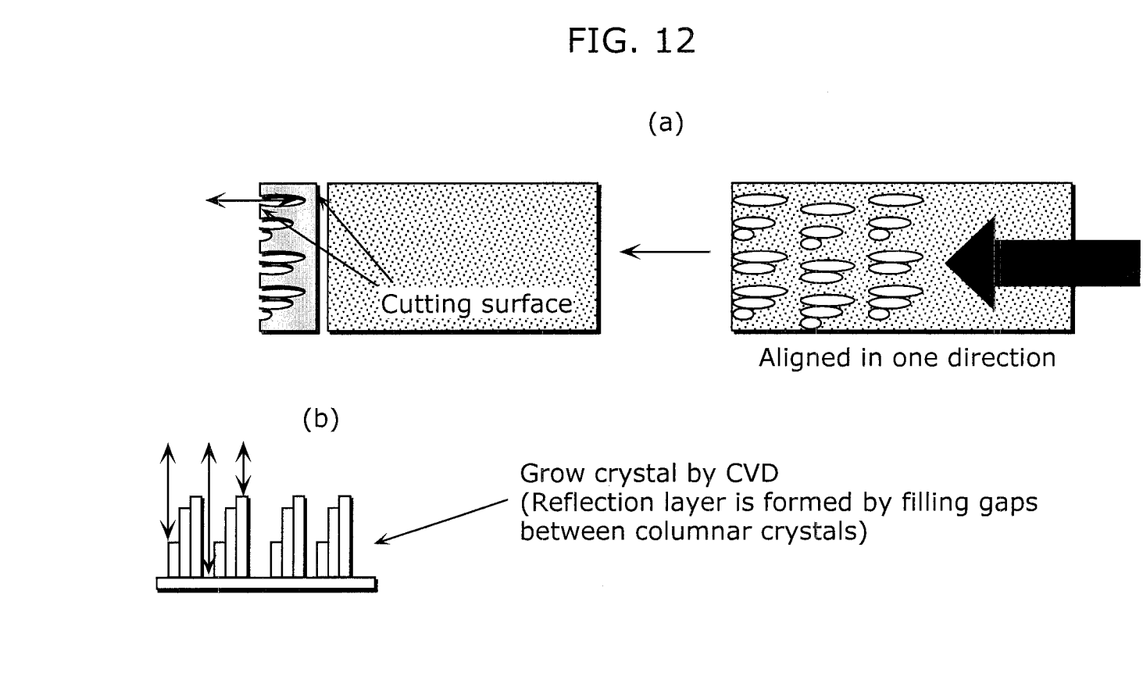
Figure 14C:
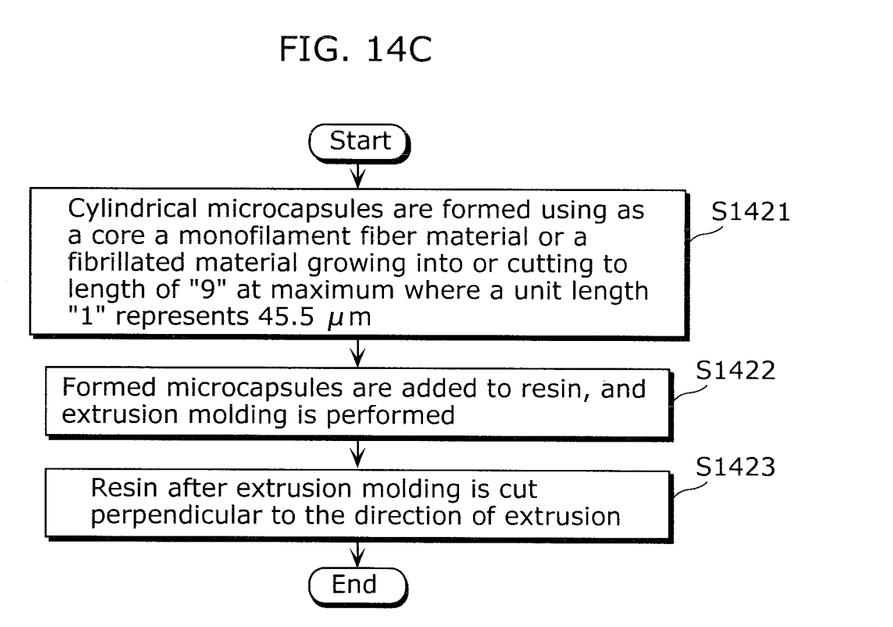
FIG. 14C is a flowchart showing steps for forming a backing layer in which cylindrical microcapsules are used as acoustic tubes.

FIGS. 12 (a) and (b) are diagrams showing a method of forming a backing layer in which microcapsules are used as acoustic tubes. FIG. 12 (a) is a diagram showing a method of extrusion molding for a resin mixed with cylindrical microcapsules. FIG. 12 (b) is a diagram showing a method of growing columnar crystals on a board by CVD. FIG. 14C is a flowchart showing steps for forming the backing layer in which cylindrical microcapsules are used as acoustic tubes. Here, a crystal is to be grown while the length of the columnar crystals is being controlled by CVD (Chemical Vapor Deposition) method or through the use of a carbon nanotube. Alternatively, using as a core a carbon fiber or a carbon nanotube of which the length is thus controlled, a microballoon may be formed.

In order to realize the backing layer 4 according to Embodiment 5, cylindrical microcapsules are formed by performing, on metal alkoxide which includes Si or the like, hydrolysis and polycondensation (sol-gel reaction) within an aqueous and/or oily solution, and firing the resulting columnar porous material. Here, the core of the metal alkoxide is a monofilament fiber material or a fibrillated material that is prepared by growing into or cutting to a length of 9 at maximum based on Embodiment 2 wherein a unit length "1" represents 45.5 μm (S1421). The formed microcapsules are added to a resin at predetermined blending ratio, and the extrusion molding is performed (S1422). The resin after the extrusion molding is cut along a plane perpendicular to the direction of the extrusion, and thus obtained material is used as a backing (S1423). As shown in FIG. 12 (a), performing the extrusion molding on the resin which is mixed with microcapsules has an effect of aligning the longitudinal direction of the cylindrical microcapsules with the direction of a flow of the resin. Thus, by cutting the resin board after the extrusion molding such that the cutting plane becomes perpendicular to the flow direction as shown in the left-hand diagram of FIG. 12 (a), the acoustic tubes of different depths with the same bore diameter can be exposed on the surface part of the board. Furthermore, instead of the microcapsules, it is possible to grow columnar crystals on the board and fill the gaps between the grown columnar crystals in order to form a reflection layer, and thereby form a backing layer 4 having the portion of the columnar crystals as the acoustic tubes 5. Growing the columnar crystals by CVD method or the like allows the length of the columnar crystals to be controlled, and thus it is possible to form the acoustic tubes 5 which are arranged precisely based on Embodiment 2.

Figure 13:
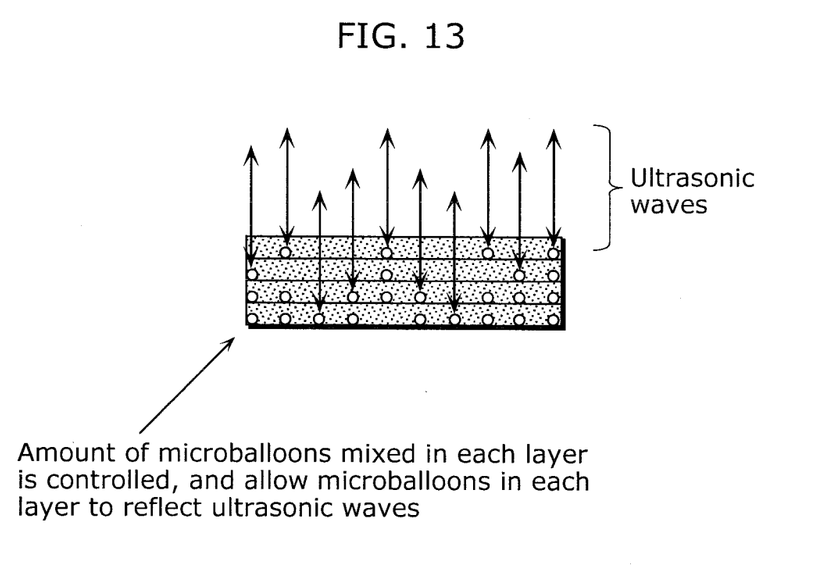
FIG. 13 is a diagram showing a method of forming a backing layer in which spherical microballoons are used.

In addition, the backing layer according to this embodiment may also be realized by cutting the grooves or pores. Further, the similar effect can be expected by forming a backing layer by stacking resin layers such that spherical microballoon particles disposed within the resin layer are disposed continuously in a stacking direction, corresponding to the longitudinal direction of the acoustic tube 5. FIG. 13 is a diagram showing a method of forming the backing layer 4 in which spherical microballoons are used. First, using resins in which spherical microballoons are uniformly mixed at predetermined various ratios, two or more types of resin layers are formed. The resin layers thus formed with different mixture densities are stacked in a predetermined order such that the microballoons are disposed continuously in the stacking direction, corresponding to the length of the acoustic tubes 5. With this, the backing layer 4 formed from the stacked resin layers as shown in FIG. 13 can be formed.

It is to be noted that although the cases where the shape of the cross section of each acoustic tube is either a square or a circle have been described as exemplary embodiments in the above, the cross section of each acoustic tube may be in any shape such as oval, triangle, or hexagon.

By using the acoustic tubes 5 disposed as described above, the reflected waves in the backing layer 4 can be attenuated, and thus the sensitivity of the ultrasonic transducer can be increased. Also, heat can be released to outside of the backing layer 4 using the acoustic tubes, and thus the heat contained in the backing layer 4 can be dissipated.

INDUSTRIAL APPLICABILITY

The present invention is useful for reducing reflected waves in a backing layer of an ultrasonic transducer, and increasing a sensitivity of a received ultrasonic wave signal. In addition, the present invention is useful in realizing a thinner ultrasonic transducer, and reducing a cost of manufacturing as a result of the thinner ultrasonic transducer.

| 1 | Piezoelectric transducer |
| 2 | Matching layer |
| 3 | Acoustic lens |
| 4 | Backing layer |
| 5 | Acoustic tube |

The invention claimed is:

1. An ultrasonic transducer comprising:
a vibrating element which emits ultrasonic waves; and
a backing material which is provided in contact with a back side of said vibrating element and which attenuates ultrasonic waves that are emitted toward the back side of said vibrating element and have an opposite phase to a phase of ultrasonic waves emitted toward a front side of said vibrating element,
wherein acoustic tubes are disposed in said backing material such that a longitudinal direction of each of said acoustic tubes is in line with a traveling direction of the ultrasonic waves which are emitted by said vibrating element and travel toward the front side and the back side, said acoustic tubes having mutually different lengths on the basis of a principle of an acoustic wave synthesis, and
said acoustic tubes attenuate in whole or in part the ultrasonic waves emitted by said vibrating element toward said backing material.

2. The ultrasonic transducer according to claim 1,
wherein said backing material includes, instead of said acoustic tubes, reflectors equivalent to said acoustic tubes.

3. The ultrasonic transducer according to claim 1,
wherein said acoustic tubes are aligned in an order of integer n in a linear direction on a plane where said backing material contacts an other layer, and
said acoustic tubes are disposed such that a length Ln of said each acoustic tube satisfies Equation 2 where c denotes a speed of sound, N denotes a prime number, n denotes an integer which varies in a range of 0 to (N−1), and wr denotes any design frequency:

[Math. 1]

$$Ln = \frac{c \cdot n^2 (\text{mod } N)}{2N\omega r} \quad \text{(Equation 2)}$$

4. The ultrasonic transducer according to claim 1,
wherein said acoustic tubes are aligned in an order of integer n in a linear direction on a plane where said backing material contacts an other layer, and
said acoustic tubes are disposed such that a length Ln of said each acoustic tube satisfies Equation 3 where c denotes a speed of sound, N denotes a prime number, n denotes an integer which varies in a range of 0 to (N−1), r denotes a primitive root of N, and wr denotes any design frequency:

[Math. 2]

$$Ln = \frac{c \cdot r^n (\text{mod } N)}{2(N-1)\omega r} \quad \text{(Equation 3)}$$

5. The ultrasonic transducer according to claim 1,
wherein said backing material includes microcapsules and curable polymeric resin, and
reflectors equivalent to said acoustic tubes are said microcapsules which are distributed in said polymeric resin.

6. The ultrasonic transducer according to claim 5,
wherein each of said microcapsules is of a spherical or cylindrical shape obtained by providing an outer shell to a base material through sol-gel reaction, the base material being made of a monofilament fiber of predetermined length.

7. The ultrasonic transducer according to claim 5,
wherein each of said microcapsules is of a cylindrical shape, and
the reflectors equivalent to said acoustic tubes are said cylindrical microcapsules which are disposed such that said cylindrical microcapsules are aligned lengthwise.

8. An ultrasonic diagnostic apparatus comprising the ultrasonic transducer according to claim 1.

9. A method of forming a backing material used in an ultrasonic transducer,
the ultrasonic transducer comprising:
a vibrating element which emits ultrasonic waves; and
the backing material which is provided in contact with a back side of the vibrating element and which attenuates ultrasonic waves that are emitted toward the back side of the vibrating element and have an opposite phase to a phase of ultrasonic waves emitted toward a front side of the vibrating element,
wherein acoustic tubes are disposed in the backing material such that a longitudinal direction of each of the acoustic tubes is in line with a traveling direction of the ultrasonic waves which are emitted by the vibrating element and travel toward the front side and the back side, the acoustic tubes having mutually different lengths on the basis of a principle of an acoustic wave synthesis, and
the acoustic tubes attenuate in whole or in part the ultrasonic waves emitted by the vibrating element toward the backing material,
said method comprising:
preparing mixtures of microcapsules and curable polymeric resin, each of the mixtures having a different microcapsule inclusion ratio; and
forming the backing material by stacking resin layers formed from the mixtures each having the different microcapsule inclusion ratio, and by subsequently curing and molding the stacked resin layers into a predetermined shape.

10. The method of forming a backing material according to claim 9,
wherein each of the microcapsules is formed to have a spherical or cylindrical shape by providing an outer shell to a base material through sol-gel reaction, the base material being made of a monofilament fiber of predetermined length.

11. A method of forming a backing material used in an ultrasonic transducer,
the ultrasonic transducer comprising:
a vibrating element which emits ultrasonic waves; and
the backing material which is provided in contact with a back side of the vibrating element and which attenuates ultrasonic waves that are emitted toward the back side of the vibrating element and have an opposite phase to a phase of ultrasonic waves emitted toward a front side of the vibrating element,
wherein acoustic tubes are disposed in the backing material such that a longitudinal direction of each of the acoustic tubes is in line with a traveling direction of the ultrasonic waves which are emitted by the vibrating element and travel toward the front side and the back side, the acoustic tubes having mutually different lengths on the basis of a principle of an acoustic wave synthesis, and
the acoustic tubes attenuate in whole or in part the ultrasonic waves emitted by the vibrating element toward the backing material, said method comprising:

preparing a mixture of microcapsules and curable polymeric resin; and forming the backing material by performing extrusion molding on the mixture to cause the microcapsules to be aligned lengthwise in the mixture and curing the mixture.

12. The method of forming a backing material according to claim 11, wherein each of the microcapsules is formed as a material of a cylindrical shape by providing an outer shell to a base material through sol-gel reaction, the base material being made of a monofilament fiber of predetermined length.

13. The method of forming a backing material according to claim 12, wherein there are two or more lengths in a longitudinal direction for the microcapsules.

* * * * *